(12) United States Patent
He et al.

(10) Patent No.: US 10,751,194 B2
(45) Date of Patent: Aug. 25, 2020

(54) BIONIC DISLOCATION-PROOF ARTIFICIAL LUMBAR VERTEBRAE AND DISC COMPLEX

(71) Applicant: XI'AN JIAOTONG UNIVERSITY, Xi'an, Shaanxi (CN)

(72) Inventors: Xijing He, Shaanxi (CN); Jiantao Liu, Shaanxi (CN); Feng Zhang, Shaanxi (CN); Gaole He, Shaanxi (CN)

(73) Assignee: XI'AN JIAOTONG UNIVERSITY, Xi'an, Shaanxi (CN)

( * ) Notice: Subject to any disclaimer, the term of this patent is extended or adjusted under 35 U.S.C. 154(b) by 0 days.

(21) Appl. No.: 15/762,833

(22) PCT Filed: Dec. 5, 2016

(86) PCT No.: PCT/CN2016/108539
§ 371 (c)(1),
(2) Date: Mar. 23, 2018

(87) PCT Pub. No.: WO2017/185754
PCT Pub. Date: Nov. 2, 2017

(65) Prior Publication Data
US 2018/0263788 A1    Sep. 20, 2018

(30) Foreign Application Priority Data
Apr. 29, 2016  (CN) .......................... 2016 1 0285603

(51) Int. Cl.
*A61F 2/44*      (2006.01)
*A61F 2/30*      (2006.01)

(52) U.S. Cl.
CPC ........ *A61F 2/4425* (2013.01); *A61F 2/30771* (2013.01); *A61F 2/442* (2013.01); *A61F 2002/3065* (2013.01); *A61F 2002/30125* (2013.01); *A61F 2002/30126* (2013.01); *A61F 2002/30168* (2013.01);
(Continued)

(58) Field of Classification Search
CPC ............................................... A61F 2/44–447
See application file for complete search history.

(56) References Cited

U.S. PATENT DOCUMENTS 5,236,460 A * 8/1993 Barber .................... A61F 2/441
                                                   403/109.7
5,360,430 A * 11/1994 Lin .......................... A61F 2/44
                                                   606/247

(Continued)

*Primary Examiner* — Nicholas J Plionis

(57) ABSTRACT

The bionic dislocation-proof artificial lumbar vertebrae and disc complex comprises vertebral body components, intervertebral disc components and screws; the vertebral body components comprise an oval column; the intervertebral disc components comprise L-shaped arc plates and composite pads, the L-shaped arc plates comprise bottom plates, lateral plate and the raised column; end of the raised column is the ball shell with two raised arc; the composite pad is connected to the groove on the oval column; the ball shell and the composite ball form the ball and socket joint. The present invention replaces the removed vertebrae and adjacent discs and maintains the rotation, flexion and extension and buffer function, which ensures the stability and mobility of the lumbar spine after surgery. The present invention better resembles the normal physiology.

4 Claims, 9 Drawing Sheets

(52) U.S. Cl.
CPC ............... *A61F 2002/30177* (2013.01); *A61F 2002/30205* (2013.01); *A61F 2002/30331* (2013.01); *A61F 2002/30405* (2013.01); *A61F 2002/30545* (2013.01); *A61F 2002/30563* (2013.01); *A61F 2002/30578* (2013.01); *A61F 2002/30649* (2013.01); *A61F 2002/30662* (2013.01); *A61F 2002/30784* (2013.01); *A61F 2002/30827* (2013.01); *A61F 2002/30841* (2013.01); *A61F 2002/30904* (2013.01); *A61F 2002/443* (2013.01); *A61F 2310/00023* (2013.01); *A61F 2310/00796* (2013.01)

(56) References Cited

U.S. PATENT DOCUMENTS

| | | | | |
|---|---|---|---|---|
| 5,556,431 A * | 9/1996 | Buttner-Janz | ......... | A61F 2/4425 606/247 |
| 6,899,735 B2 * | 5/2005 | Coates | ...................... | A61F 2/44 623/17.11 |
| RE42,480 E * | 6/2011 | Bryan | ................... | A61B 17/686 606/247 |
| 8,696,749 B2 * | 4/2014 | Lyons | ..................... | A61F 2/442 623/17.12 |
| 9,655,735 B2 * | 5/2017 | Baynham | ................ | A61F 2/442 |
| 2005/0197703 A1 * | 9/2005 | Diaz | .................... | A61F 2/4425 623/17.13 |
| 2005/0216081 A1 * | 9/2005 | Taylor | ....................... | A61F 2/44 623/17.11 |
| 2007/0100456 A1 * | 5/2007 | Dooris | .................. | A61F 2/4425 623/17.14 |
| 2008/0015704 A1 * | 1/2008 | Gradl | ....................... | A61F 2/44 623/17.16 |
| 2010/0106251 A1 * | 4/2010 | Kast | ....................... | A61F 2/442 623/17.16 |
| 2012/0130497 A1 * | 5/2012 | Taylor | ....................... | A61F 2/44 623/17.16 |
| 2012/0197400 A1 * | 8/2012 | Lei | ........................... | A61F 2/44 623/17.14 |

* cited by examiner

BIONIC DISLOCATION-PROOF ARTIFICIAL LUMBAR VERTEBRAE AND DISC COMPLEX

CROSS REFERENCE OF RELATED APPLICATION

This is a U.S. National Stage under 35 U.S.C. 371 of the International Application PCT/CN2016/108539, which claims priority under 35 U.S.C. 119(a-d) to CN 201610285603.X, filed Apr. 29, 2016.

BACKGROUND OF THE PRESENT INVENTION

Field of Invention

The present invention relates to manufacture field of medical prosthesis, and more particularly to a lumbar vertebrae and adjacent intervertebral disc transplant. The bionic dislocation-proof artificial lumbar vertebrae and disc complex preserves the lumbar spine mobility.

Description of Related Arts

The lumbar spine locates on lower section of the spine. The vertebral body is large. The upper and lower endplates of the vertebrae are in a kidney-shape. The back of the endplate is slightly concave. The vertebral body is connected to the adjacent vertebral body by the intervertebral disc which is wide in the front and narrow in the rear. The adjacent vertebraes and discs form a physiological curvature which bears most of the weight of the human body. The intervertebral discs assist the vertebrae for a rotation, lateral bending, flexion and extension to a certain degree. Studies have shown that the range of motion in flexion-extension of the whole lumbar spine of healthy Chinese people are between 14.15°-29.39° for the male and 14.54°-26.61° for the female (overlay method).

The spinal tuberculosis, tumor and old fracture easily lead to scoliosis, spinal compression and other complications which severely threaten human health. Debridement of the lesions followed by interbody fusion with a titanium mesh cage combined with transplantation of bone has become a common treatment for these diseases above. The surgical approaches are divided into simple anterior approach, simple posterior approach and combined anterior and posterior approach. The treatments are widely used by spinal surgeons due to instant and long-term stability. The fusion impairs the motion function of at least three fused vertebral bodies, which concentrates stress and increases the range of motion of the non-fusion sections and leads to complications such as adjacent intervertebral discs degeneration, secondary spinal stenosis, zygapophyseal joint degeneration, acquired spondylolisthesis, spinal instability and etc. Some scholars have long followed up studies and found that patients with titanium cage fusion with bone grafting may have complications such as titanium cage subsidence which need further treatments.

In order to overcome the shortcomings of the titanium cage, improvements on artificial vertebral body draws intense attention. The aritificial vertebral body has been developed into support—fixed type, adjust fixed type and self fixed type, and the material is developed from metal into ceramics, polymer composites and etc. Although the development of the artificial vertebral body improves the stability and a certain prosthesis even removes the nail-stick system to reduce the surgical wound, the prosthesis is fixed mainly by fusion which compromise the normal vertebral motion function and is not able to avoid the possible complications. Artificial vertebral body with a certain motion function has been developed by some researchers, the motion center of which is near the center of the vertebral body and away from the intervertebral space. The motion range of the artificial vertebral body is small and does not agree with the normal physiology of the spine, which induces facet joint abrasion, calcification and other unpredictable potential complications. Thus, the artificial vertebral body with a certain motion function is not widely applied on the patients.

In order to maintain the motion function of the vertebrae, researches on artificial intervertebral disc have been carried out by domestic and foreign researchers. Conventionally, there are multiple artificial intervertebral discs applied in treatments of cervical and lumbar disc diseases; wherein the SB Charité Disc and Prodisc II is widely applied in treatments of lumbar disc diseases. In a prospective randomized control research, the implant of SB Charité Disc achieves a better treatment effect in low back pain than internal fixation such as fusion with bone grafting. Researches show a possible prosthesis shift and dislocation after the implant of intervertebral disc, which leads to damages of the adjacent blood vessels and nerves and cause spine instability for multi-stage artificial intervertebral disc implants. The patients with vertebral body disease are not able to be implanted with the artificial intervertebral discs.

In order to solve the problems, professor He Xijing, Lei Wei and et al. carry out researches on artificial lumbar vertebrae and disc system and achieve progresses in cervical spine. The bionic atlantoaxial prosthesis, the artificial vertebrae and disc complex of lower cervical spine have achieved satisfying results in animal studies. The anatomy and function of the lumbar vertebrae are too complicated to adopt the artificial cervical vertebrae and disc complex. The artificial lumbar vertebrae and disc complex must satisfy the below requirements: 1. guarantee the instant and long-term stability of the spine after the implant; 2. maintain the motion function of the adjacent vertebrae; 3. meet the needs for bearing weight as a normal spine. The conventional prosthesis, artificial discs and artificial cervical vertebrae and disc system are not able to meet the requirements. No reports disclose the artificial lumbar vertebrae and disc complex in domestic and foreign literature.

SUMMARY OF THE PRESENT INVENTION

An object of the present invention is to overcome the problem of the conventional fusion technology, which borrows the advantages and overcomes the disadvantages of the conventional artificial intervertebral disc and vertebral body. The present invention provides a bionic dislocation-proof artificial lumbar vertebrae and disc complex.

The present invention adopts the following technical solution.

The bionic dislocation-proof artificial lumbar vertebrae and disc complex comprises vertebral body components and intervertebral disc components on two ends of the vertebral body; wherein the intervertebral disc components comprise L-shaped arc plates and composite pads, the L-shaped arc plates comprise bottom plates and lateral plate which match endplates and sides of the vertebral body components vertebral body components respectively; wherein the lateral plates are on the bottom plates; the bottom plates are connected to the composite pads by ball and socket joints; wherein the vertebral body components vertebral body components comprise oval columns; there are grooves on two ends of the oval columns; the two composite pads are embedded in grooves on corresponding ends of the oval columns respectively.

An edge of each of the bottom plates comprises an open ellipse two ends of which are smoothly transit to an M-shaped curve; wherein the open ellipse is symmetrically along a minor axis of a corresponding ellipse; each of the lateral plate is on the open ellipse at the edge of each of the bottom plates; each of the lateral plate tilts inwardly and form an angle of 70-80 degree with a corresponding bottom plate; on each of the lateral plate there are screw holes.

There are an oval top and conic teeth on the bottom plates; the oval top, the conic teeth and one of the lateral plate (10) are on a same side of the corresponding bottom plate; a center of the oval top is coincide with a center of the corresponding bottom plate; a height of the oval top diminishes from a center to an edge; the conic teeth are distributed along an ellipse edge of the oval top at intervals on the corresponding bottom plate.

There are two screw holes which are not on a same horizontal plane.

Each of the composite pads comprises a lower oval column embedded in a corresponding groove on an end of the oval column, an upper oval column on an opening of the groove, which is connected to the lower oval column, and a composite ball acts as an articular head of the ball and socket joint; wherein an arc groove with a round opening is on the upper oval column; the arc groove (14) extends to the lower oval column; the composite ball is in the arc groove; there is a gap between the composite ball and the upper oval column; there is a spherical shell in the gap to match with the composite ball as an articular nest; the spherical shell is connected to a raised column on each of the bottom plates.

There are two raised arcs on an opening edge of the ball shell; the two raised arcs are opposite to each other; two notches are on a wall of the arc groove; the two notches are opposite to each other; a distance between exterior walls of the two raised arcs is not bigger than a distance between the two notches and bigger than a diameter of the round opening of the arc groove.

The two raised arc are symmetrical along a sagittal plane; the two notches are symmetrical along a coronal plane.

The raised column comprises a bigger column which is connected to the bottom plate and a smaller column which is connected the bigger column; the ball shell is connected to the smaller column; a centre line of the bigger column coincides with a centre line of the smaller column; an edge of bigger column and smaller column contact area are rounded; a top of the composite ball is higher than the upper oval column; an outer edge of the upper oval column and a corresponding side of the bottom plate is rounded; an inner edge of the upper oval column and the corresponding side of the bottom plate (at the arc groove with a round opening) is a tapered enlargement.

There are a certain number of small round grooves randomly distributed on the oval column; two rectangle through grooves are crossed on a center of the oval column; the two rectangle through grooves travel along a sagittal plane and a coronal plane respectively.

The oval column, the L-shaped arc plate and the composite pad are integrated into one body; the oval column and the L-shaped arc plate adopt medical titanium alloy; the composite pad adopts UHMWPE (ultra-high molecular weight polyethylene) or PEEK (polyetheretherketone); hydroxylapatite coating is applied on a contact area of the L-shaped arc plate and bones and a flank of the oval column.

There is an arc concave A on a side of the oval column goes through the oval column along an axial direction; there is an arc concave B on a side of a lower oval column goes through the lower oval column along an axial direction; the arc concave A and the arc concave B are in a same shape.

There is a limit groove on a side of a lower oval column of each of the composite pads; a sawtooth structure A is on an internal wall of the limit groove; the limit groove is symmetrical along a mid-sagittal plane of the lower oval column and passes through the arc groove; a limit composite pad is inside the limit groove; a first side of the limit composite pad matches the composite ball; a second side of the limit composite pad matches an exterior wall of each of the composite pads; a sawtooth structure B is on a side of the limit composite pad; the sawtooth structure B matches the sawtooth structure A; the limit groove acts with the limit composite pad to form a limit component.

A size of the limit groove and the limit composite pad is adjustable.

The limit composite pad adopts medical UHMWPE or PEEK.

The benefits of the present invention are as follow.

1. The ball shell with raised arcs casted by the titanium alloy and the composite ball made by polyethylene or polyetheretherketone form the dislocation-proof ball and socket joint, which centers the motion in the intervertebral space center and avoids potential complications caused by range center heterotopia. The rotation, lateral bending, flexion, extension and part of the buffer function of the spine are remained, which resembles the normal physiology.

2. The shape of the bottom plate of the L-shaped arc plate is similar to the front of the endplates of the lumbar vertebrae. The oval top matches the concave at the back of center of the lumbar vertebrae endplates. Conic teeth are on the upper part and edge of the oval top, which fasten and fix the bottom plate with the endplates. The lateral plate of the L-shaped arc plate is closely fit with the sides of the vertebrae to enlarge the contact area, which effectively avoids the stress concentration. The raised bigger column on the bottom plate is able to bear the transverse shear stress caused by flexion and extension and avoid adverse events such as deformation, break and etc.

3. Small round grooves are distributed randomly on the sides of the vertebral body components, which promote surrounding tissue attachment and remnant bone ingrowth. The two rectangle through grooves in the middle contain much implanted bone, which help the fusion of the surrounding tissue and guarantee a mobility and stability.

4. Hydroxylapatite coating is applied on a contact area of the L-shaped arc plate and bones and sides of the vertebral body components, which helps the fusion of the surrounding tissue and guarantees a mobility and stability.

5. Two screw holes not at the same level are set on the lateral plate of the L-shaped arc plate. The screws are implanted in different directions to fix the lateral plate to the neighboring vertebral body and reduce the risk of dislocation.

6. The rotation range around the axis of the dislocation-proof ball and socket joint is controlled by adjusting the limiting component. The facet joint and surrounding soft tissue injuries caused by excessive axis rotation are thus avoided.

Figure 1:
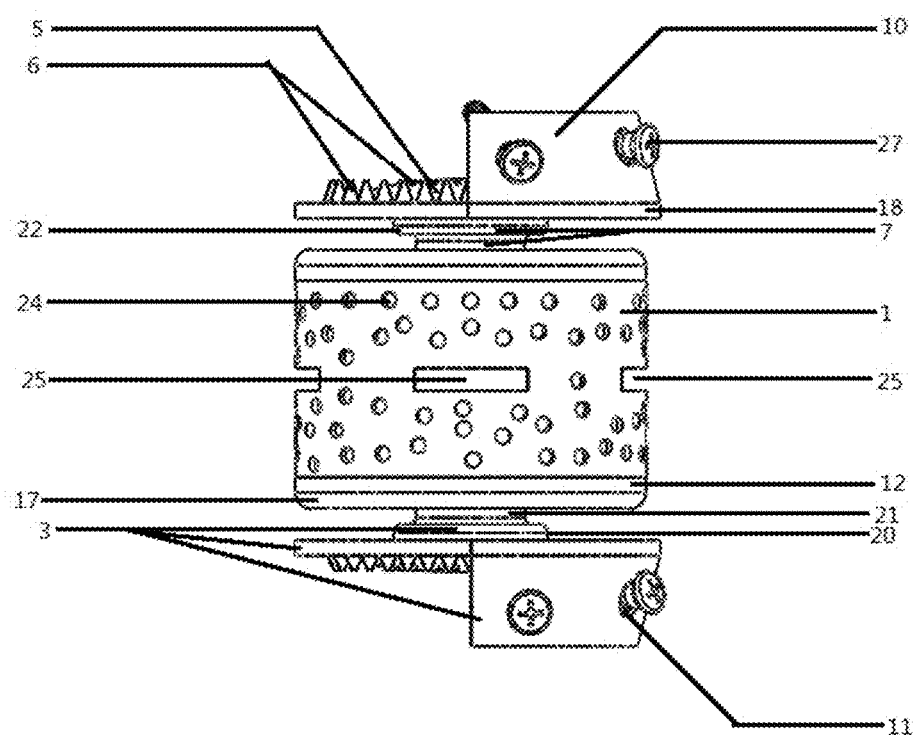
FIG. 1 is a front view of the present invention.
Figure 2:
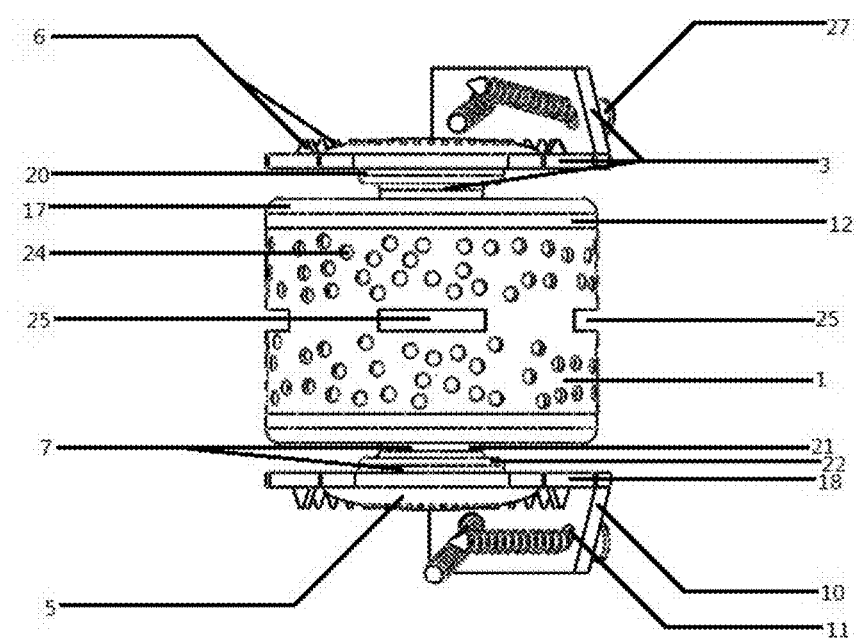
FIG. 2 is a rear view of the present invention.
Figure 3:
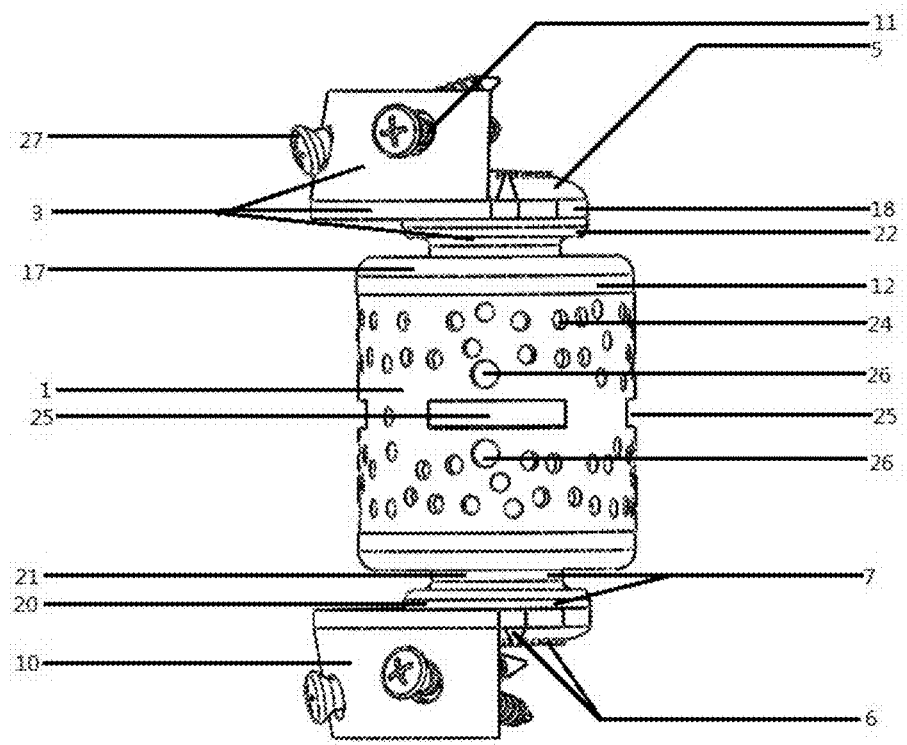
FIG. 3 is a side view of the present invention.
Figure 4:
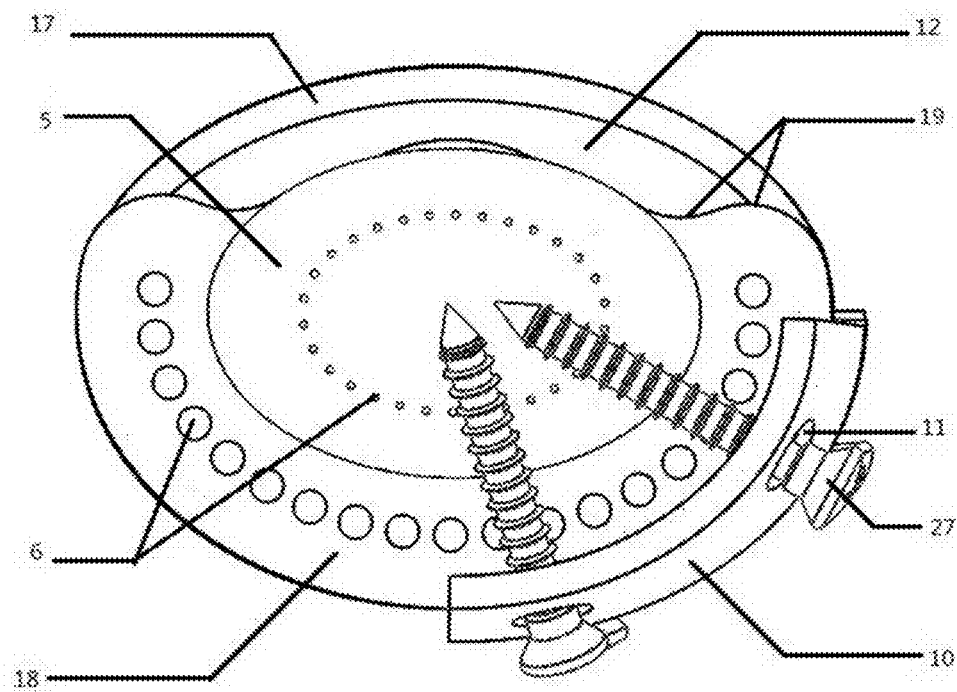
FIG. 4 is a top view of the present invention.
Figure 5:
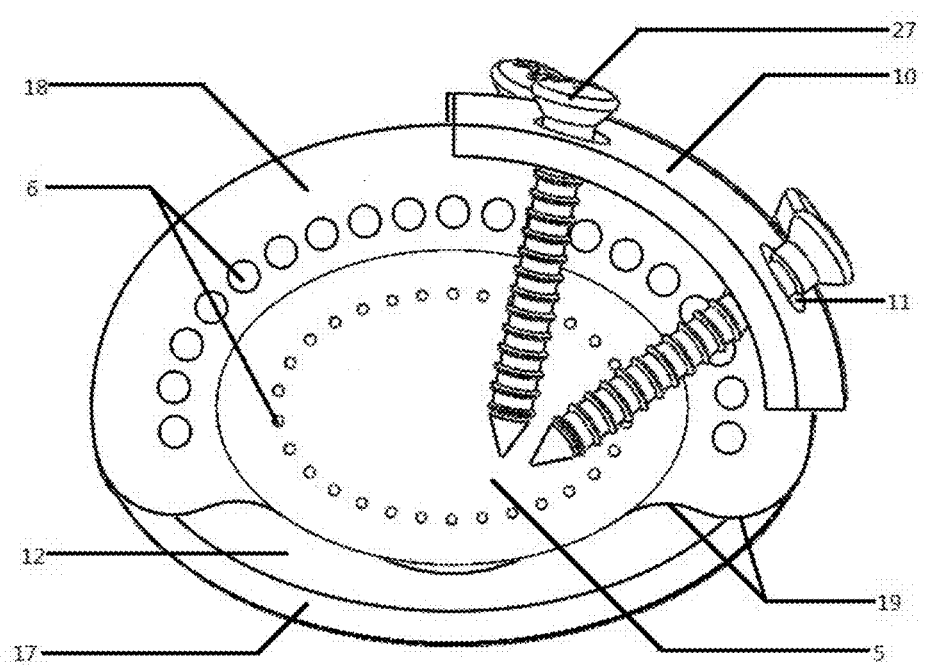
FIG. 5 is a bottom view of the present invention.

Element number: 1. oval column; 2. groove; 3. L-shaped arc plate; 4. composite pad; 5. oval top; 6. conic teeth; 7. raised column; 8. raised arc; 9. ball shell; 10. lateral plate; 11. screw hole; 12. upper oval column; 13. lower oval column; 14. arc groove; 15. the composite ball; 16. notch; 17. top edge of upper oval column; 18. bottom plate; 19. bottom plate back edge; 20. bigger column; 21. smaller column; 22. edge of bigger column and smaller column contact area; 23. arc groove opening; 24. small round groove; 25. rectangle through groove; 26. column groove; 27. screw; 28. arc concave A; 29. arc concave B; 30. limit groove; 31. sawtooth structure A; 32. limit composite pad; 33. sawtooth structure B.

DETAILED DESCRIPTION OF THE PREFERRED EMBODIMENT

Referring to the drawings, according to a preferred embodiment of the present invention is illustrated in detail.

Referring to FIG. 1 to FIG. 10 and FIG. 14 to FIG. 17, the bionic dislocation-proof artificial lumbar vertebrae and disc complex comprises lumbar vertebrae components, intervertebral disc components and screws 27; wherein the vertebral body components comprise an oval column 1 with grooves 2 on top and bottom ends; there is an arc concave 28 which passes through the oval column 1 along the axis; small round grooves 24 are randomly distributed on the side of the oval column; two rectangle through grooves 25 are in the middle of oval column 1; the two rectangle grooves travel along the a sagittal plane and coronal plane respectively; the small round groove promotes the surrounding tissue attachment; the two rectangle through grooves 25 are able to contain implanted bones; two column grooves 26 is set symmetrically on top and bottom ends of the opening of the rectangle through groove along the coronal plane, which are convenient for the surgeon to hold the complex while surgery; the intervertebral disc components comprise L-shaped arc plates 3 which are connected to the adjacent vertebral body and composite pads 4 which are connected to the vertebral body components, the L-shaped arc plates 3 comprise bottom plates 18, lateral plate 10 and raised column 7; the bottom plate 18 is in a super-oval shape; a bottom plate back edge 19 is rounded; an oval top 5 and conic sawteeth 6 are set on a contact area of the bottom plate and an adjacent endplates; a center of the oval top 5 coincides with a center of the bottom plate 18; a height of the oval top diminishes from the center to the edge; the conic sawteeth 6 are evenly distributed along the oval edge on the bottom plate 18 at intervals; the raised column 7 is on the oval center of a relative area of the bottom plate 18 and the composite pad 4; the raised column 7 comprises a bigger column 20 which is near the bottom plate 18 and a smaller column 21 which is away from the bottom plate 18; a centre line of the bigger column 20 and the smaller column 21 are coincided; the edge of the contact area of the bigger column and the smaller column 22 is rounded; the end of the smaller column 21 comprises a ball shell 9 with two raised arcs 8; the raised arcs are distributed symmetrically on two sides of the ball shell along a sagittal plane; the cross section of the lateral plate 10 is a quarter of an oval; the lateral plate 10 is on the left front edge of the bottom plate 18 and gradually tilts inward; two screw holes 11 which are not at the same level are set on the lateral plate 10; the L-shaped arc plate 3 is firmly fixed on the sides of the adjacent vertebras by screws 27; the composite pad 4 comprises upper and lower oval column; there is an arc groove 14 around the centre line of the upper column 12; an arc concave B 29 passes through the lower oval column along an axis; the shape of an arc concave A 28 on a side of the oval column 1 is same as the arc concave B 29; a limit groove 30 is on the side of the lower column 13; sawtooth structure A 31 is on an internal wall of the limit groove 30; the limit groove 30 is symmetrically distributed along a mid-sagittal plane of the lower column 13 and passes through arc groove 14; a limit composite pad 32 is in the limit groove; a first side of the composite pad 32 matches the composite ball 15; a second side of the composite pad 32 matches an exterior wall of the composite pad; the sawtooth structure B 33 is on a side of the limit composite pad 32; the sawtooth structure B 33 matches the sawtooth structure A 31 on the internal wall of the limit groove 30 to prevent the limit component from loose and dislocation; the limit groove 30 matches the limit composite pad 32 to form the limit component; a size of the limit groove 30 and the limit composite pad 32 is adjustable; the rotation range of the ball and socket joint along the axis is adjusted the size of the limit groove 30 and the limit composite pad 32, wherein the rotation range of the ball and socket joint is 0-90°; the inner wall of the arc groove 14 is an the composite ball structure; two notches 16 are on the front and back of the outer wall of the arc groove 14; the two notches 16 are symmetrically distributed on the outer wall of the arc groove 14 along the coronal plane; the top of the the composite ball 15 on the inner wall of the arc groove 14 is higher than the upper oval column 12; the opening of the arc groove 14 is a tampered enlargement which ensures flexion and extension while limit excessive motion; an outer diameter of the opening of the arc groove 14 is smaller than the distance between an exterior wall of the two raised arcs 8 on the sub-hemisphere ball shell; the distance between the notches 16 is same as the distance between the exterior wall of the two raised arcs 8; the two raised arcs 8 is able to be set in the arc groove 14; the raised arcs are rotated away from the notches to embed the limit composite pad 32 in the lower column 13 by the limit groove 30, which prevents the dislocation of the ball shell 9 from the arc groove 14 and limit the rotation range of the ball and socket joint; The stability of the ball and socket joint is guaranteed and the facet joint and surrounding soft tissue injuries caused by excessive rotation are avoided; the lower oval column 13 of the composite pad 4 is in the groove 2 on the oval column 1, which effectively prevents the dislocation of the composite pad 4 from the groove; the top edge of the upper oval column 17 is rounded; the ball shell 9 matches the composite ball 15 to form the ball and socket joint which ensures the rotation, lateral bending, flexion and extension function after the surgery; the screws 27 is in screw holes; the lower oval column of the composite pad is connected to the groove 2 of the vertebral body components which ensures the stability of the bionic artificial lumbar vertebrae and disc complex.

Figure 6:
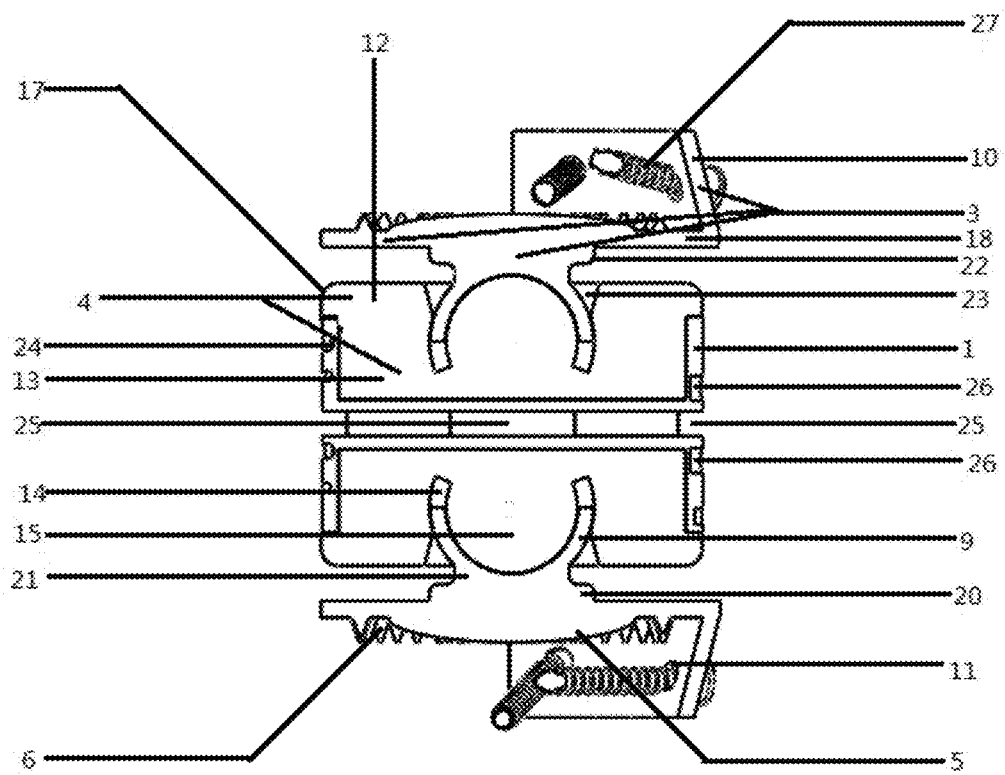
FIG. 6 is a profile along a coronal plane.
Figure 7:
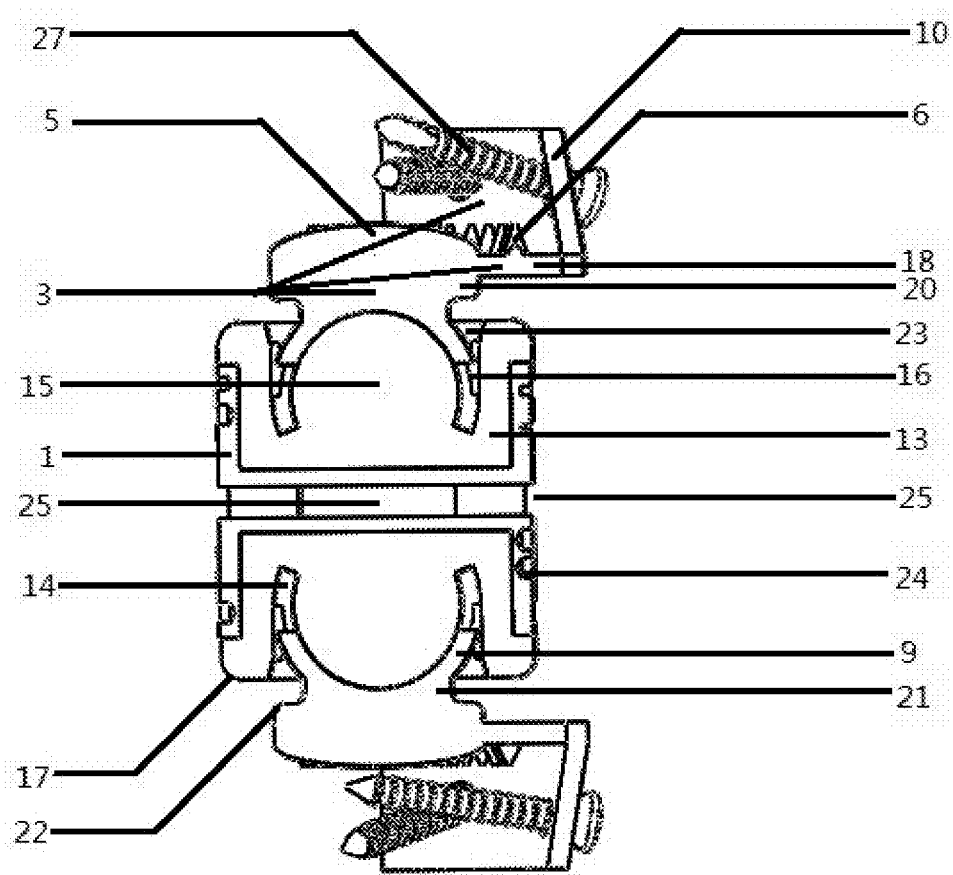
FIG. 7 is a profile along a sagittal plane.

Referring to FIG. 6 and FIG. 7, the arc groove 14 is the space for placing the ball shell 9.

The vertebral body components, the L-shaped arc plate 3 and the screws 27 adopt medical titanium alloy and are integrated into one body. The hydroxylapatite coating is applied on the contact area (such as the top of the bottom plate and the internal surface of the lateral plate) between the L-shaped arc plate 3 and the cortical bone and the sides of the vertebral body components, which ensure the stability after the surgery. The composite pad 4 adopts UHMWPE (ultra-high molecular weight polyethylene) or PEEK (polyetheretherketone) and is integrated into one body. The limit composite pad 32 also adopts UHMWPE or PEEK. The inner and outer wall of the arc groove 14 and the inner and outer wall of ball shell 9 are polished, which effectively reduce friction on the contact area.

Figure 10:
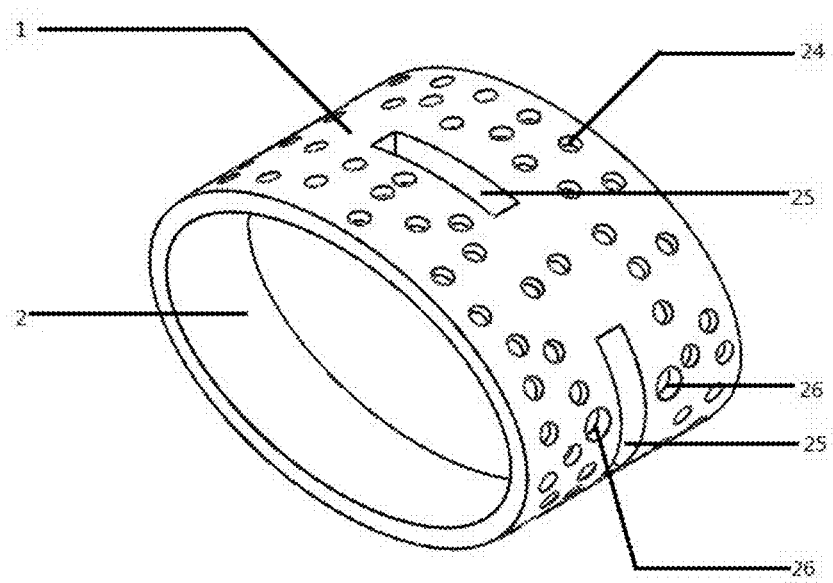
FIG. 10 is an isometric view of vertebral body components.

Referring to the FIG. 10, the height of the oval column 1 is 26 mm; the semi-major axis of the oval is 23 mm; the semi-minor axis is 15 mm; the depth of the grooves on two end of the oval column 1 is 10 mm; the semi-major axis of the groove is 21 mm; the semi-minor axis of the groove is 13 mm; the opening of the two rectangle through groove 25 on the side of the oval column 1 is 3 mm*15 mm; the depth of the small round grooves 24 which are distributed randomly on the oval column 1 is 1 mm; the radius of the small round grooves 24 is 1 mm; the depth of column groove 26 is 1.5 mm; the radius of the column groove 26 is 1.5 mm.

Figure 8:
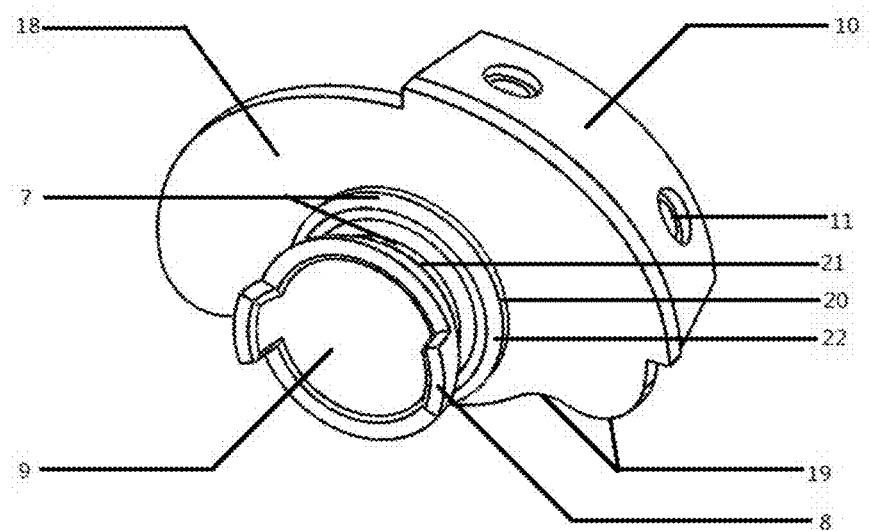
FIG. 8 is an isometric view of an L-shaped arc plate.
Figure 11:
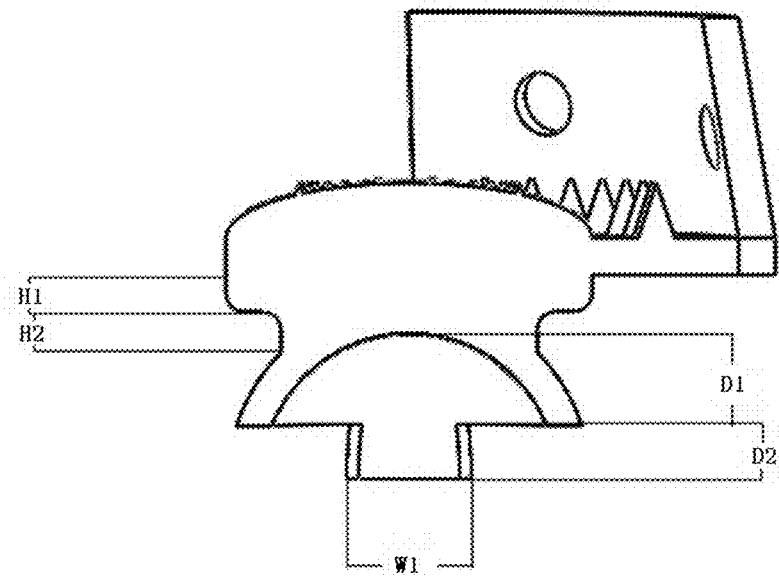
FIG. 11 is a Schematic diagram shows parameters of the L-shaped arc plate.

Referring to the FIG. 8 and the FIG. 11, the thickness of the bottom plate 18 of the L-shaped arc plate 3 is about 2 mm; the bottom plate 18 is in a super-oval shape with an arc of 225°; the semi-major axis of the oval is 23 mm; the semi-minor axis of the oval is 18 mm; the bottom plate back edge is rounded with a radius of 5 mm; the height of the center of the oval top 5 on the bottom plate 18 is 2 mm; the height of the oval top 5 diminishes from the center to the edge; the semi-major axis of the oval top 5 is 15 mm; the semi-minor axis of the oval top 5 is 10 mm; the center of the oval top 5 coincides with the center of the bottom plate 18; the height of the conic teeth 6 on the bottom plate is 0.5 mm; the radius of the bottom of the conic teeth 6 is 0.25 mm (part of the conic teeth are illustrated in the drawings); the thickness of the lateral plate 10 on the L-shaped arc plate is about 2 mm; the cross-section of the lateral plate 10 is a quarter of an oval; the height of the lateral plate 10 is 12 mm; the lateral plate 10 tilt inwardly and form an angle of 70-80 degree with a corresponding bottom plate 18; the radius of the screw hole 11 is 2 mm; the height of the raised column 7 is 5 mm; the height of the bigger column 20 is H1=2 mm; the height of the smaller column 21 is H2=3 mm; the radius of the bigger column is 10 mm; the radius of the smaller column is 7 mm; the edge of the contact area of the bigger column and smaller column is rounded with a radius of 1 mm; the thickness of the ball shell at the end of the smaller column is about 2 mm; the internal radius of the ball shell is 8.1 mm; the distance between the plane of the opening of the ball shell and the top of the ball shell is D1=5.1 mm; the distance between the bottom plane of the two raised arcs 8 and opening plane of the ball shell is D2=3 mm; the width of each of the raised arcs 8 is W1=6.8 mm.

Figure 9:
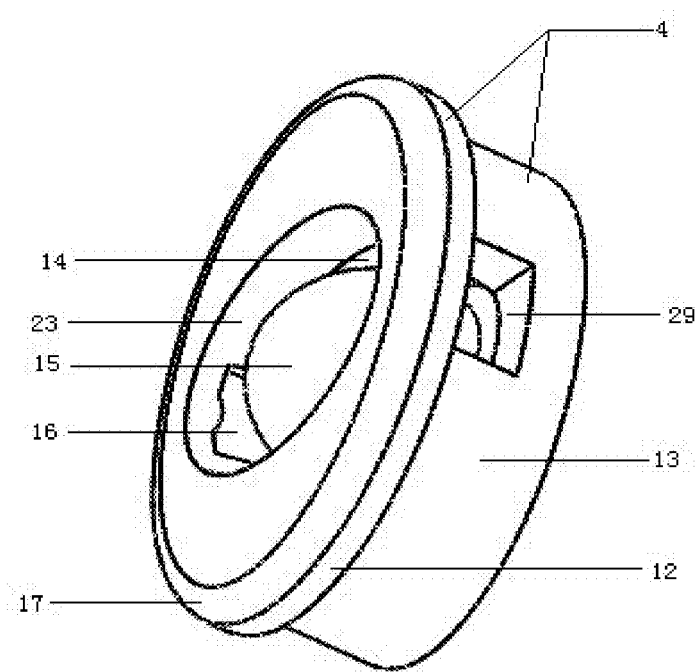
FIG. 9 is an isometric view of a composite pad.
Figure 12:
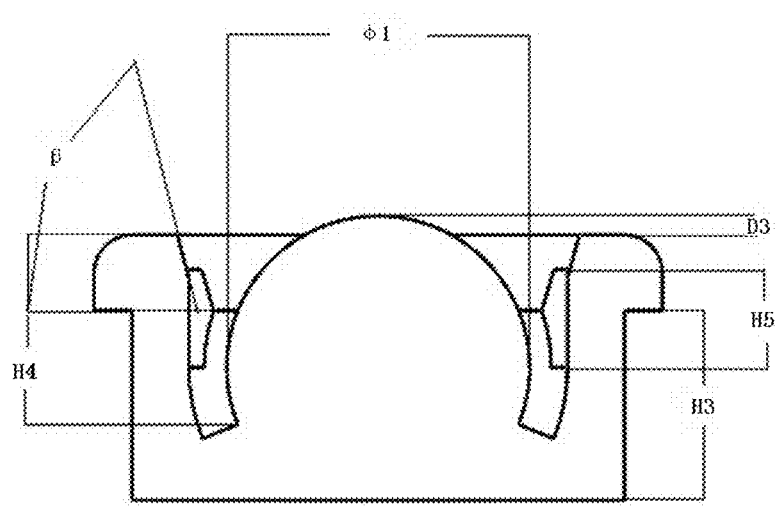
FIG. 12 is a Schematic diagram shows parameters of the composite pad.

Referring to the FIG. 9 and the FIG. 12, the height of the upper oval column 12 on the composite pad 4 is 3 mm; the height of the lower oval column 13 is H3=10 mm; the semi-major axis of the upper oval column 12 is 23 mm; the semi-minor axis of the upper oval column 12 is 15 mm; the semi-major axis of the lower oval column 13 is 21 mm; the semi-minor axis of the lower oval column 13 is 13 mm; the top edge of the upper oval column is rounded with a radius of 2 mm; the width of the arc groove 14 is 2.0 mm; the depth of the arc groove 14 is H4=9 mm; the diameter of the composite ball is φ1=16 mm; the top of the composite ball is higher than the upper oval column 12 by a distance of D3=2 mm; the opening of the arc groove is a tapered enlargement with a taper height of 3 mm; the opening and the end of the upper oval column form an angle of 75 degree (β); the depth of each of the notches 16 on the front and back of the arc groove is H5=5.3 mm; the width of each of the notches 16 is 7 mm.

The thickness of the hydroxylapatite coating is 20 μm.

The parameters are adjustable according to the size of the lumbar vertebrae of the patients.

Figure 13:
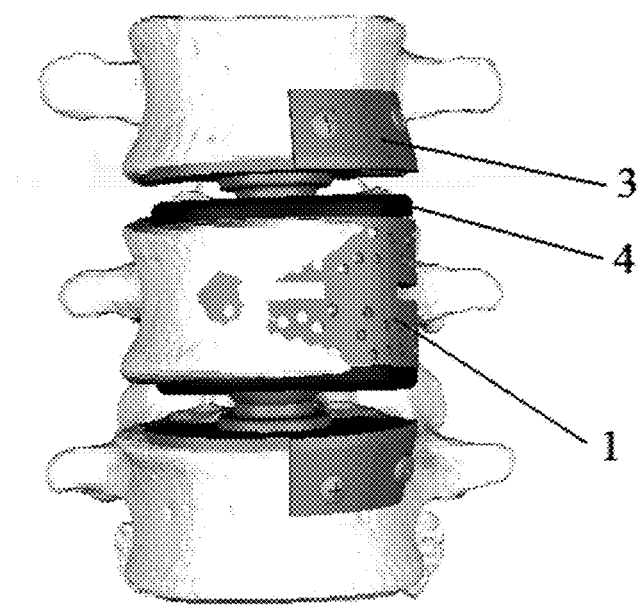
FIG. 13 is a perspective view of an implant of a bionic dislocation-proof artificial lumbar vertebrae and disc complex.
Figure 14:
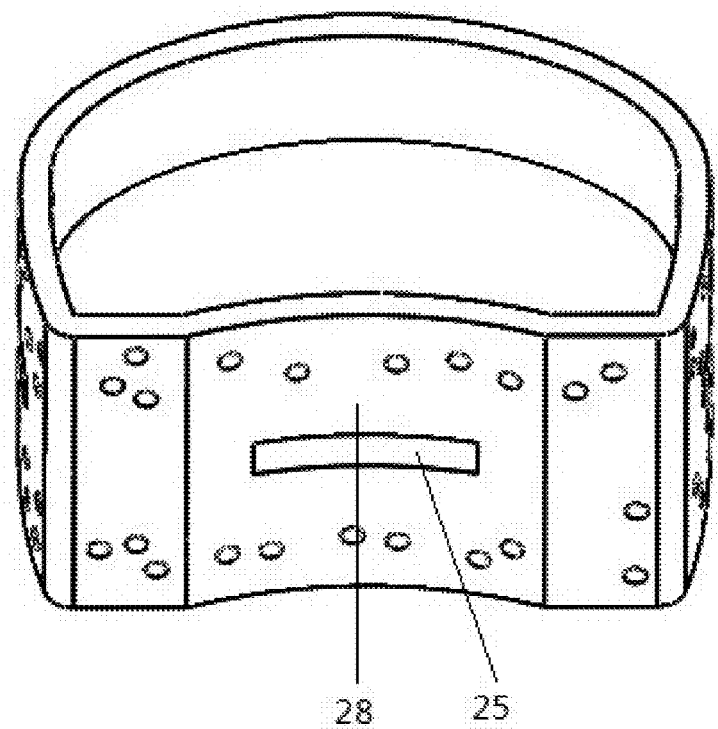
FIG. 14 is an isometric view of the vertebral body components in another embodiment.
Figure 15:
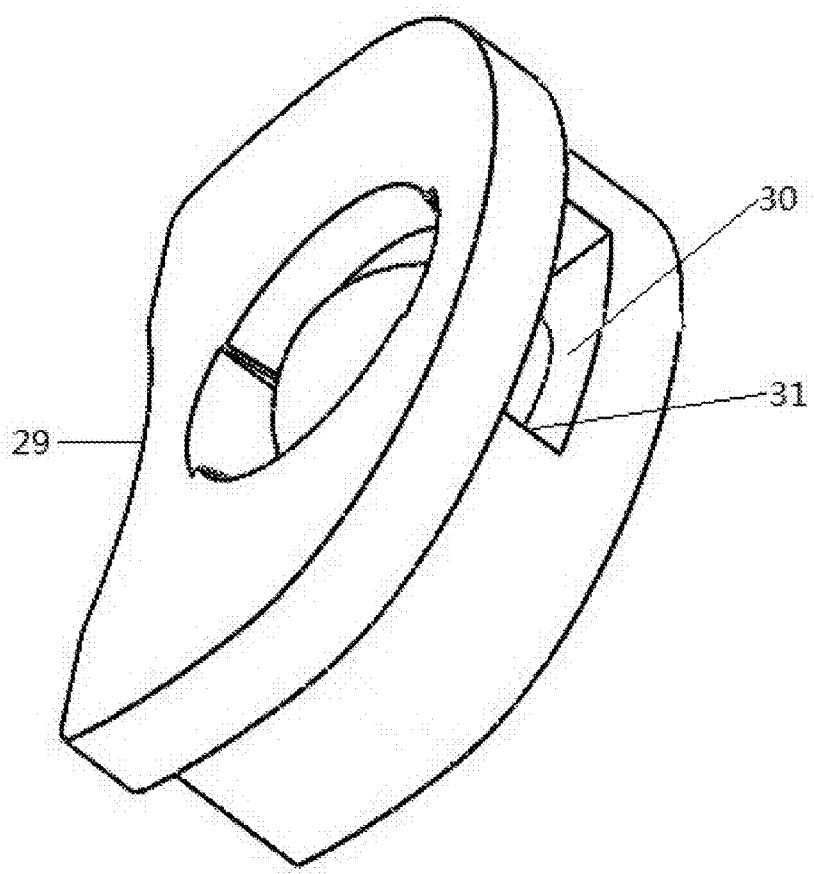
FIG. 15 is an isometric view of the composite pad in another embodiment.
Figure 16:
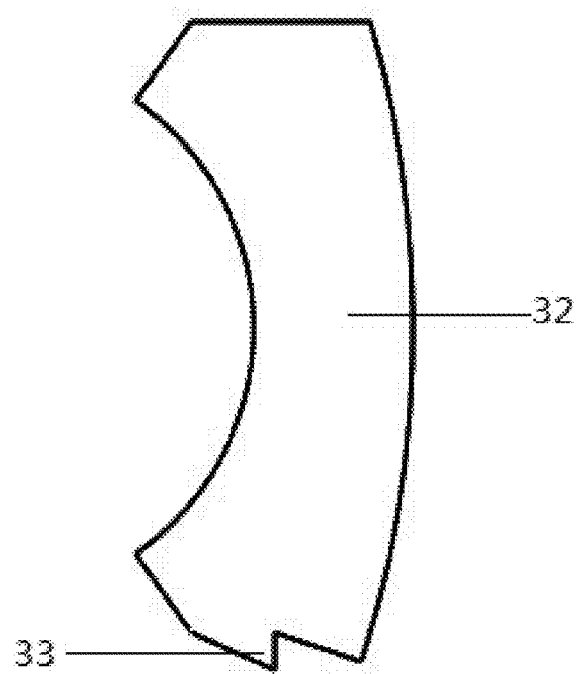
FIG. 16 is a top view of a limit composite pad.
Figure 17:
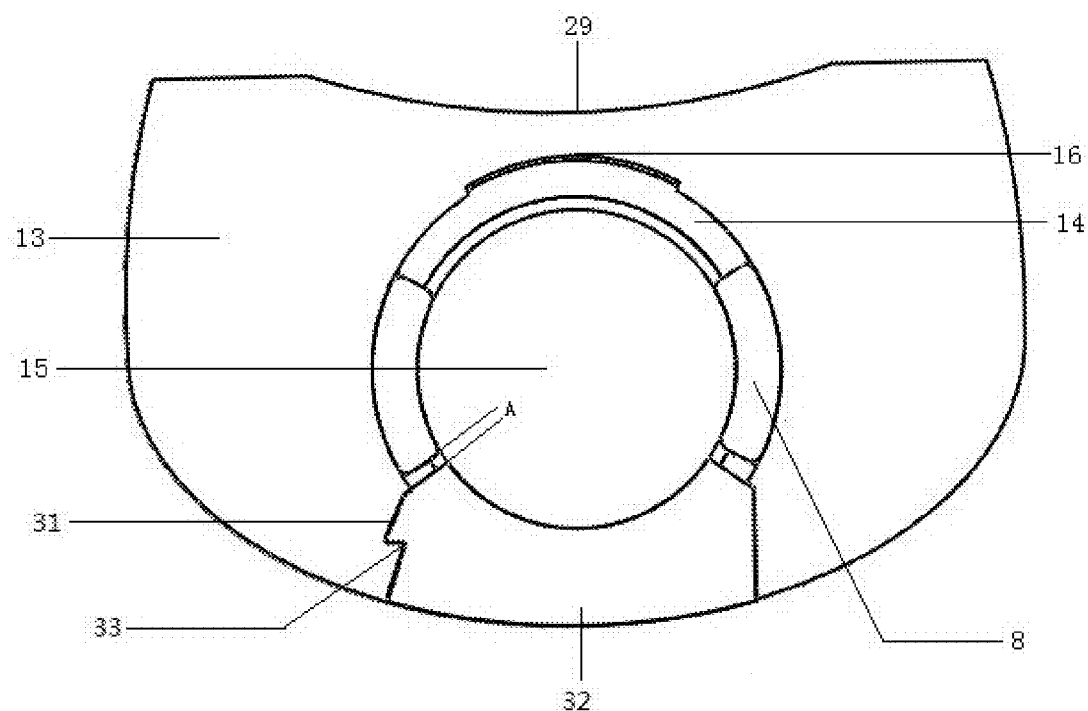
FIG. 17 is a cross-section of a ball and socket joint.

Referring to the FIG. 13, the bionic dislocation-proof artificial lumbar vertebrae disc complex is assembled in the following way, wherein the lower oval column 13 of the composite pad 4 is placed in the groove 2 of the oval column 1; the ball shell 9, the raised arc 8 and the arc groove 14 form the dislocation-proof ball and socket joint; the contact areas of the ball and socket joint are highly polished to reduce the friction and abrasion while the joint motions; the L-shaped arc plate 3 is fixed on the adjacent vertebras by the screws 27 and the screw holes 11; the shape of the bottom plate 18 of the L-shaped arc is similar to the endplates; the oval top 15 matches the concave of the endplates; the conic teeth 6 further fix the bottom plate 18 on the adjacent endplates; the lateral plate 10 expands the contact area with the adjacent vertebra, effectively reduces the stress concentration and guarantee the bearing function of the lumbar vertebrae; the rectangle through grooves 25 are on the oval column 1 and the small round grooves 24 are randomly distributed on the oval column 1, which promotes the surrounding tissue attachment and growth; the long-term stability of the spine after the surgery is thus ensured. The dislocation-proof ball and socket joint guarantees the stability of the intervertebral disc after the implant, prevents the dislocation of the prothesis and limits the rotation range of the prothesis along the axis. The rotation, lateral bending, flexion and extension function of the lumbar spine are maintained, which better resembles the normal physiology.

The bionic dislocation-proof artificial lumbar vertebrae and disc complex disclosed comprises a vertebral body components, intervertebral disc components and screws 27; wherein the vertebral body components comprise an oval column 1 with grooves 2 on top and bottom ends; small round grooves 24 are randomly distributed on and two rectangle through grooves 25 are in the oval column 1; the intervertebral disc components comprise L-shaped arc plates 3 which are connected to the adjacent lumbar vertebra and composite pads 4 which are connected to the vertebral body components, the L-shaped arc plates 3 comprise bottom plates 18, lateral plate 10 and raised column 7; an oval top 5 and conic sawteeth 6 are on the bottom plate; two screw holes 11 which are on different planes are set on the lateral plate 10; the end of the raised column 7 is a ball shell 9 with two raised arcs 8; each of the composite pads 4 comprises upper and lower oval column; the lower oval column 13 is in the groove of the oval column 1; an arc groove 14 is around the centre line of the upper column 12; the inner side of the arc groove 14 is the composite ball 15; the ball shell and the composite ball on the upper oval column form the ball and socket joint; the joint surface is polished and the contact area with bone is hydroxylapatite coated. The present invention replaces the removed vertebrae and adjacent discs and maintains the rotation, flexion and extension and buffer function, which ensures the stability and mobility of the spine after surgery. The present invention better resembles the normal physiology.

What is claimed is:

1. A bionic dislocation-proof artificial lumbar vertebrae and disc complex, comprising: an implant and vertebral disc prostheses on two ends of the implant: wherein each of the vertebral disc prostheses comprises L-shaped arc brackets (3) and composite pads (4), wherein the L-shaped arc brackets (3) comprises bottom plates (18) and lateral plates (10) which match endplates and sides of vertebras respectively: wherein the lateral plates (10) are on the bottom plates (18): the bottom plates (18) are connected to the composite pads (4) by ball and socket joints; wherein the implant comprises oval columns (1); there are concave grooves (2) on two ends of the oval columns (1); the two composite pads (4) are embedded in the concave grooves (2) respectively; wherein each of the composite pads (4) comprises a lower oval column (13) embedded in a corresponding concave groove (2), an upper oval column (12) on an opening of the corresponding concave groove (2), and a composite ball acts as an articular head of the ball and socket joint; wherein an arc trough (14) with a round opening is on the upper oval column (12); the arc trough (14) extends to the lower oval column (13); the composite ball is in the arc trough (14); there is a gap between the composite ball and the upper oval column (12); there is a ball shell in the gap to match with the composite ball as an articular nest; and the ball shell is connected to a raised column (7) on each of the bottom plates (18); wherein the raised column (7) comprises a bigger column (20) which is embedded in the bottom plate (18) and a smaller column (21) which is embedded in the bigger column (20); the ball shell is stuck to the smaller column(21); a center line of the bigger column (20) coincides with a center line of the smaller column (21); an edge of a contact area of the bigger column (20) and the smaller column (21) is rounded; and a top of the composite ball is higher than the upper oval column (12).

2. A bionic dislocation-proof artificial lumbar vertebrae and disc complex, comprising: an implant and vertebral disc prostheses on two ends of the implant; wherein each of the vertebral disc prostheses comprises L-shaped arc brackets (3) and composite pads (4), wherein the L-shaped arc brackets (3) comprises bottom plates (18) and lateral plates (10) which match endplates and sides of vertebras respectively; wherein the lateral plates (10) are on the bottom plates (18); the bottom plates (18) are connected to the composite pads (4) by ball and socket joints; wherein the implant comprises oval columns (1); there are concave grooves (2) on two ends of the oval columns (1); the two composite pads (4) are embedded in the concave grooves (2) respectively; wherein each of the composite pads (4) comprises a lower oval column (13) embedded in a corresponding concave groove (2), an upper oval column (12) on an opening of the corresponding concave groove (2), and a composite ball acts as an articular head of the ball and socket joint; wherein an arc trough (14) with a round opening is on the upper oval column (12); the arc trough (14) extends to the lower oval column (13); the composite ball is in the arc trough (14); there is a gap between the composite ball and the upper oval column (12); there is a ball shell in the gap to match with the composite ball as an articular nest; and the ball shell is connected to a raised column (7) on each of the bottom plates (18);wherein there is a limit trough (30) on a side of the lower oval column (13) of each of the composite pads (4); a sawtooth structure A (31) is on an internal wall of the limit trough (30); the limit trough (30) is symmetrical along a sagittal plane of the lower oval column (13) and passes through the arc trough (14); a limit composite pad (32) is inside the limit trough (30); an interior side of the limit composite pad (32) matches the composite ball (15); an outer side of the limit composite pad (32) matches an exterior wall of each of the composite pads (4); a sawtooth structure B (33) is on a side of the limit composite pad (32); the sawtooth structure B (33) matches the sawtooth structure A (31); and the limit trough (30) acts with the limit composite pad (32) to form a limit component.

3. The bionic dislocation-proof artificial lumbar vertebrae and disc complex, as recited in claim 1, wherein a size of the limit trough (30) and the limit composite pad (32) is adjustable.

4. The bionic dislocation-proof artificial lumbar vertebrae and disc complex, as recited in claim 1, wherein the limit composite pad (32) adopts medical UHMWPE (ultra-high molecular weight polyethylene) or PEEK (polyetheretherketone).

* * * * *